(12) United States Patent
Coolbaugh et al.

(10) Patent No.: US 6,312,672 B1
(45) Date of Patent: Nov. 6, 2001

(54) SUNSCREEN COMPOSITIONS CONTAINING COPOLYMERS OF ISOPRENE BUTADIENE AND/OR STYRENE TO PROVIDE IMPROVED WATER RESISTANCE

(75) Inventors: Thomas S. Coolbaugh, Yardley, PA (US); Sandra S. Davis, North Brunswick, NJ (US); John E. Marlin, II, Bridgewater, NJ (US); Demetreos N. Matthews, Edison, NJ (US); Fahimeh P. Shirazi, Belle Mead, NJ (US)

(73) Assignee: Exxon Mobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/429,947

(22) Filed: Oct. 29, 1999

(51) Int. Cl.$^7$ .............. A61K 7/42; A61K 7/44; A61K 31/74; A61K 7/00
(52) U.S. Cl. .......... 424/59; 424/60; 424/78.02; 424/78.08; 424/400; 424/401
(58) Field of Search ............... 424/59, 60, 400, 424/401, 78.02, 78.08

(56) References Cited

U.S. PATENT DOCUMENTS

| | | |
|---|---|---|
| 3,954,897 | 5/1976 | Yamato et al. . |
| 4,061,780 | 12/1977 | Yoshida et al. . |
| 4,122,023 | 10/1978 | Yasui et al. . |
| 4,522,807 | 6/1985 | Kaplan . |
| 4,663,157 | 5/1987 | Brock . |
| 4,668,505 | 5/1987 | Grollier et al. . |
| 4,710,371 | 12/1987 | Palinczar . |
| 4,900,543 | 2/1990 | Ritter et al. . |
| 4,900,544 | 2/1990 | Ritter et al. . |
| 4,925,653 | 5/1990 | Grollier et al. . |
| 5,019,378 | 5/1991 | Allen . |
| 5,145,669 | 9/1992 | Kwak et al. . |
| 5,160,730 | 11/1992 | Dubief et al. . |
| 5,204,090 | 4/1993 | Han . |
| 5,223,250 | 6/1993 | Mitchell et al. . |
| 5,330,747 | 7/1994 | Krzysik . |
| 5,385,729 | 1/1995 | Prencipe et al. . |
| 5,399,342 | 3/1995 | Krzysik . |
| 5,451,610 | 9/1995 | Krzysik . |
| 5,460,804 | 10/1995 | Krzysik . |
| 5,487,885 | 1/1996 | Sovak et al. . |
| 5,494,657 | 2/1996 | Swenson . |
| 5,505,935 | 4/1996 | Guerrero et al. . |
| 5,512,272 | 4/1996 | Krzysik . |
| 5,531,985 | 7/1996 | Mitchell et al. . |
| 5,599,533 | 2/1997 | Stepniewski et al. . |
| 5,633,415 | 5/1997 | Brandes et al. . |
| 5,653,965 | 8/1997 | Narayanan et al. . |
| 5,707,612 | 1/1998 | Zofchak et al. . |
| 5,711,939 | 1/1998 | Brunke et al. . |
| 5,756,082 | 5/1998 | Cashin et al. . |
| 5,833,973 | 11/1998 | Dobkowski et al. . |
| 5,849,314 | 12/1998 | Dobkowski et al. . |
| 5,876,699 | * 3/1999 | Di Somma et al. ............ 424/59 |

FOREIGN PATENT DOCUMENTS

| | | | |
|---|---|---|---|
| 0461497 A1 | 12/1991 | (EP) | ............ A61K/7/48 |
| 06 080856 A | 3/1994 | (JP) . | |

* cited by examiner

*Primary Examiner*—Shelley A. Dodson

(57) ABSTRACT

The invention provides waterproof sunscreen compositions which include polymers of isoprene, butadiene and/or styrene, particularity conjugated dienes which may be subject to some degree of hydrogenation. A copolymer of two different conjugated dienes is preferred. The polymers may be selectively hydrogenated to produce polymers which have highly controlled amounts of unsaturation, thereby improving water resistance.

7 Claims, No Drawings

SUNSCREEN COMPOSITIONS CONTAINING COPOLYMERS OF ISOPRENE BUTADIENE AND/OR STYRENE TO PROVIDE IMPROVED WATER RESISTANCE

BACKGROUND OF THE INVENTION

This invention is directed to sunscreen formulations comprising copolymers of isoprene, butadiene and or styrene which have improved water resistance. More particularly, this invention is directed to sunscreen formulations comprising liquid block copolymers having unsaturation only on the terminal blocks and methods of preparation thereof for use in sunscreen.

U.S. Pat. No. 5,204,090 describes waterproof sunscreens comprising a water insoluble film forming polymer. U.S. Pat. No. 5,653,965 describes film forming polymers for sunscreen spray. U.S. Pat. No. 5,487,886 describes acryl polymers for sunscreen formulations. U.S. Pat. No. 5,145,669 describes water proof sunscreens containing a crosslinked, neutralized terpolymer of maleic anhydride, a C1–C5 alkyl vinyl ether and a C12–C14 alpha-olefin monomer. U.S. Pat. No. 4,663,157 describes a copolymer of ethylene and acrylic acid for use in sunscreen compositions.

Sunscreen products are usually applied prior to activities such as bathing or sports. The product will remain effective after exposure to water and/or perspiration. The use of water insoluble active sunscreen ingredients is usually insufficient to provide adequate water resistance. A thickener also is required in such formulations. However, an effective method of accomplishing water resistance or water proofing of a sunscreen formula is to employ a water-insoluble substantive film forming resin. A Carbomer resin can provide thickening action. Typical materials for waterproofing sunscreen formulations are two resins which are copolymers of vinylpyrrolidone and long chain alkanes, C16 and C20. They are oil-soluble film forming polymers which have been used for some time by the cosmetic industry.

Therefore, it is the object of the present invention to provide new polymers for sunscreen formulations with improved properties.

SUMMARY OF THE INVENTION

Selectively hydrogenated low molecular weight polymers based on isoprene, butadiene and styrene are inherently immiscible in water and soluble in a wide range of organic materials including hydrocarbon and ester fluids. These polymers are useful in the preparation of sunscreen formulations containing complex mixtures of ingredients and lead to enhanced performance of active ingredients.

Sunscreen formulations rely on the presence of UV absorbers (typically organic compounds) in a mixture of organic and aqueous components. Because of the miscibility of many of the formulation components with water, UV protection may be diminished as a result of reintroduction of water following sunscreen application. This reintroduction may occur by any of several means, but two primary routes are by swimming and perspiration.

It is believed that the introduction of a non-aqueous, water-insoluble component to the sunscreen formulation would extend the effectiveness of the UV absorbers by preventing the removal upon the reintroduction of water.

The non-aqueous water-insoluble components of the present invention are polymers and copolymers of isoprene, butadiene and or styrene. Selectively hydrogenated isoprene-butadiene copolymers are preferred. The copolymers of the present invention, while providing no UV protection, have the additional advantage of being non-toxic and non-tacky when applied to skin. A choice of UV absorber may be suggested based on its solubility in the different formulation phases containing the copolymers of the present invention.

Hydrogenation of the copolymers of the present invention, selective or complete, provides oxidative stability. It is believed that the degree of hydrogenation is beneficial in the preparation of polymers with the desired refractive indices.

The invention provides sunscreen formulations which include polymers of conjugated dienes which may be partially, selectively or completely hydrogenated. The improved water resistant properties of the compositions of the invention may be controlled by controlling the size of the polymers.

In one embodiment of the invention, there is provided a sunscreen formulation comprising a copolymer of two different conjugated dienes. In this case, the first conjugated diene includes at least one relatively more substituted conjugated diene having at least five carbon atoms and the formula:

(1)

wherein $R^1$–$R^6$ are each hydrogen or a hydrocarbyl group, provided that at least one of $R^1$–$R^6$ is a hydrocarbyl group, and also provided that, after polymerization, the unsaturation of the polymerized conjugated diene of formula (1) has the formula:

(2)

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups.

The second conjugated diene in the sunscreen formulation of this embodiment includes at least one relatively less substituted conjugated diene which is different from the first conjugated diene and has at least four carbon atoms and the formula:

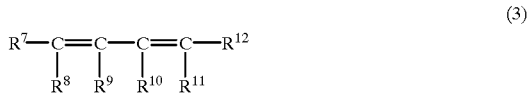

(3)

wherein $R^7$–$R^{12}$ are each hydrogen or a hydrocarbyl group, provided that, after polymerization, the unsaturation of the polymerized conjugated diene of formula (3) has the formula:

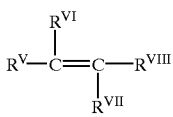

$$(4)$$

wherein $R^V$, $R^{VI}$, $R^{VII}$ and $R^{VIII}$ are each hydrogen or a hydrocarbyl group, provided that one of $R^V$ or $R^{VI}$ is hydrogen, one of $R^{VII}$ or $R^{VIII}$ is hydrogen, and at least one of $R^V$, $R^{VI}$, $R^{VII}$ and $R^{VIII}$ is a hydrocarbyl group.

Following polymerization, the diene copolymer may be partially, selectively or completely hydrogenated.

In a preferred embodiment, the sunscreen formulation includes a polymer in which the first and second conjugated dienes are polymerized as a block copolymer including at least two alternating blocks:

$$(I)_x\text{-}(B)_y \text{ or } (B)_y\text{-}(I)_x$$

In this case, the block (I) includes at least one polymerized conjugated diene of formula (1), while the block (B) includes at least one polymerized conjugated diene of formula (3). In addition, x is the number of polymerized monomer units in block (I) and is at least 1, and y is the number of polymerized monomer units in block (B) and is at least 25. It should be understood throughout that x and y are defined relative to blocks in a linear block copolymer or blocks in an arm or segment of a branched or star-branched copolymer in which the arm or segment has substantially linear structure.

Preferably, in the block copolymers of this embodiment, x is from about 1 to about 600, and y is from about 30 to about 4,000, more preferably x is from about 1 to about 350, and y is from about 30 to about 2,800. While larger values for x and y are generally related to larger molecular weights, polymers which have multiple blocks and star-branched polymers typically will have molecular weights which are not well represented in the values of x and y for each block.

Alternatively, the sunscreen formulation includes the first and second conjugated dienes polymerized as a random copolymer. The sunscreen formulation may also include the first and second conjugated dienes polymerized as a branched or star-branched copolymer.

The copolymers useful according to this embodiment typically have a molecular weight of at least about 2,000. Preferably, the molecular weight of these polymers is from above 3,000 to about 200,000, more preferably from about 5,000 to about 35,000.

In the sunscreen formulations of the invention, the copolymer is preferably selectively hydrogenated. It is preferred that the unsaturation of formula (4) be substantially completely hydrogenated, thereby retaining substantially none of the original unsaturation of this type, while the unsaturation of formula (2) is substantially retained (i.e., the residual unsaturation after hydrogenation).

After the hydrogenation reaction, the iodine Number for the residual unsaturation of formula (2) is generally from about 50% to about 100% of the Iodine Number prior to the hydrogenation reaction. More preferably, after hydrogenation, the Iodine Number for the residual unsaturation of formula (2) is about 100% of the Iodine Number prior to the hydrogenation reaction.

After the hydrogenation reaction, the Iodine Number for the residual unsaturation of formula (4) is from about 0% to about 10% of the Iodine Number prior to the hydrogenation reaction. More preferably, after the hydrogenation reaction, the iodine Number for the residual unsaturation of formula (4) is from about 0% to about 0.5% of the Iodine Number prior to the hydrogenation reaction. Most preferably, after the hydrogenation reaction, the Iodine Number for the residual unsaturation of formula (4) is from about 0% to about 0.2% of the Iodine Number prior to the hydrogenation reaction.

The conjugated diene of formula (1) preferably includes a conjugated diene such as isoprene, 2,3-dimethylbutadiene, 2-methyl-1,3-pentadiene, myrcene, 3-methyl-1,3-pentadiene, 4-methyl-1,3-pentadiene, 2-phenyl-1,3-butadiene, 2-phenyl-1,3-pentadiene, 3-phenyl-1,3 pentadiene, 2,3-dimethyl-1,3-pentadiene, 2-hexyl-1,3-butadiene, 3-methyl-1,3-hexadiene, 2-benzyl-1,3-butadiene, 2-p-tolyl-1,3-butadiene, or mixtures thereof. More preferably, the conjugated diene of formula (1) includes isoprene, myrcene, 2,3-dimethyl-butadiene or 2-methyl-1,3-pentadiene. Still more preferably, the conjugated diene of formula (1) includes isoprene.

Preferably, the conjugated diene of formula (3) includes 1,3-butadiene, 1,3-pentadiene, 1,3-hexadiene, 1,3-heptadiene, 2,4-heptadiene, 1,3-octadiene, 2,4-octadiene, 3,5-octadiene, 1,3-nonadiene, 2,4-nonadiene, 3,5-nonadiene, 1,3-decadiene, 2,4-decadiene, 3,5-decadiene, or mixtures thereof. More preferably, the conjugated diene of formula (3) includes 1,3-butadiene, 1,3-pentadiene, or 1,3-hexadiene. Still more preferably, the conjugated diene of formula (3) includes 1,3-butadiene.

Generally, when the conjugated diene includes substantial amounts of 1,3-butadiene, the polymerized butadiene includes a mixture of 1,4- and 1,2-units. The preferred structures contain at least about 25% of the 1,2-units. More preferably, the structures contain from about 30% to about 90% of the 1,2-subunits. Most preferably, the structures contain from about 45% to about 65% of the 1,2-units.

The polymers are prepared under anionic polymerization conditions. Following polymerization, the polymers of the invention are selectively hydrogenated to provide a controlled amount and extent of residual unsaturation. After the selective hydrogenation reaction, the hydrogenation catalyst is removed from the polymer.

Accordingly, as a result of the invention, there are now provided sunscreen formulations with improved water resistance. The sunscreen formulations of the invention possess numerous advantages, including prevention of hydration and resistance to water wash-off.

These and other advantages of the present invention will be appreciated from the detailed description and examples which are set forth herein. The detailed description and examples enhance the understanding of the invention, but are not intended to limit the scope of the invention.

DETAILED DESCRIPTION OF THE INVENTION

The polymer component of the sunscreen formulation of the present invention provides an effective thickener and enhanced waterproofing. Suitable polymer components include isoprene, butadiene and/or styrene homopolymers and copolymers. In one embodiment, the present invention provides sunscreen formulations comprising polymers including at least two different conjugated dienes, wherein one of the dienes is more substituted in the 2, 3, and/or 4 carbon positions than the other diene. The more substituted diene produces vinylidene, tri-, or tetra-substituted double bonds after polymerization. Hydrogenation of the material is done selectively so as to saturate the lesser substituted olefins, which primarily arise from the lesser substituted diene, while leaving a portion of the more substituted conjugated olefins behind for functionalizing.

In this embodiment, the more substituted conjugated diene will have at least five (5) carbon atoms and the following formula:

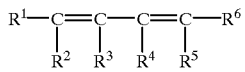

(1)

wherein $R^1$–$R^6$ are each hydrogen (H) or a hydrocarbyl group, provided that at least one of $R^1$–$R^6$ is a hydrocarbyl group. After polymerization, the unsaturation in the polymerized conjugated diene of formula (1) has the following formula:

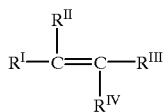

(2)

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups. Examples of conjugated dienes of formula 1 include isoprene, 2,3-dimethylbutadiene, 2-methyl-1,3-pentadiene, myrcene, and the like. Isoprene is highly preferred.

The lesser substituted conjugated diene in this embodiment differs from the other diene in that it has at least four (4) carbon atoms and the following formula:

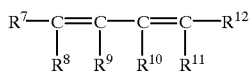

(3)

wherein $R^7$–$R^{12}$ are each hydrogen or a hydrocarbyl group. After polymerization, the unsaturation in the polymerized conjugated diene of formula (3) has the following formula:

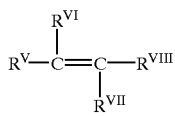

(4)

wherein $R^V$, $R^{VI}$, $R^{VII}$ and $R^{VIII}$ are each hydrogen (H) or a hydrocarbyl group, provided that one of $R^V$ or $R^{VI}$ is hydrogen, one of $R^{VII}$ or $R^{VIII}$ is hydrogen, and at least one of $R^V$, $R^{VI}$, $R^{VII}$ and $R^{VIII}$ is a hydrocarbyl group. Examples of the conjugated diene of formula (3) include 1,3-butadiene, 1,3-pentadiene, 2,4-hexadiene, and the like. A highly preferred conjugated diene of formula 3 is 1,3-butadiene.

An exception to this scheme would be when a tetra-substituted diene, e.g., 2,3-dimethylbutadiene, is used for the more substituted component. When this occurs, a tri-substituted olefin, e.g. isoprene, may be used for the lesser substituted component, such that one or both of $R^V$ and $R^{VI}$ are hydrogen and both $R^{VII}$ and $R^{VIII}$ are hydrocarbyl.

It will be apparent to those skilled in the art that in the original unsaturation of formula (2), $R^I$, $R^{II}$, $R^{III}$ and $R^{IV}$ may all be hydrocarbyl groups, whereas in the original unsaturation of formula (4) at least one of $R^V$, $R^{VI}$, $R^{VII}$ and $R^{VIII}$ must be a hydrogen.

The hydrocarbyl group or groups in the formula (1) to (4) are the same or different and they are substituted or unsubstituted alkyl, alkenyl, cycloalkyl, cycloalkenyl, aryl, alkaryl, or aralkyl groups, or any isomers thereof.

The copolymers of this embodiment are prepared by anionically polymerizing a diene of formula (1) at a level of from about 0.5% wt. to about 25% wt., and a diene of formula (3) at a level of from about 75% wt. to about 99.5% wt., in a hydrocarbon solvent using an alkyllithium catalyst. The two monomers can be polymerized in block, tapered block, or random fashion. Since the polymerization is anionic, the molecular weight distribution of these copolymers is typically very narrow, generally ranging from about 1.01 to about 1.20, and the molecular weight is determined by the ratio of monomer to initiator and/or by the presence of coupling agents. The monomers (1) and (3) may be polymerized either simultaneously or in stepwise fashion depending on the desired position of the remaining unsaturation after hydrogenation. If random positioning of the unsaturation is desired, both monomers are reacted together to give a random copolymer. If it is desirable to have the functionality on only one end, then the monomers are reacted in stepwise fashion, the order being determined as desired, to provide a diblock copolymer. If functionality is needed on both ends, then a conjugated diene of formula (1) is polymerized first, followed by a diene of formula (3). To the living anion, a coupling agent, e.g., phenyl benzoate or methyl benzoate, is then added to yield a desired triblock copolymer. Alternatively, a diene of formula (1) may be added to the living diblock to give the triblock.

A fourth approach would allow the functionality to be positioned in the center of the polymer chain. In this case, a diene of formula (3) is polymerized first, followed by a diene of formula (1). Then a triblock is formed by addition of a coupling agent or by addition of more diene of formula (3). In addition, combinations of the above approaches may be employed.

The invention can include polymers of differing microstructures. The presence of polar modifier increases the activity of the catalyst and, therefore, increase the level of 1,2-microstructure over 1,4-microstructure in polybutadiene, for example. The percentage of vinyl obtained is directly proportional to the concentration of the modifier employed. Since the reaction temperature also plays a role in determining the microstructure of polybutadiene, the level of modifier must be chosen taking into account the combined effects. Antkowiak et al., *Temperature and Concentration Effects on Polar-modified Alkyl Lithium Polymerizations and Copolymerizations, Journal of Polymer Science: Part A*-1, 10:1319–34 (1972), incorporated herein by reference have presented a way for quickly determining the proper conditions for preparation of any 1,2-microstructure content within a range of from about 10% to about 80%. Use of this method or any others to achieve the desired microstructure will be known to anyone who is skilled in the art.

The sunscreen formulations of the invention can include different polymer macrostructures. Polymers may be prepared and utilized having linear and/or nonlinear, e.g., star-branched, macrostructures. The star-branched polymers can be prepared by addition of divinylbenzene or the like to the living polymer anion. Lower levels of branching can be obtained through the use of tri-functional or tetra-functional coupling agents, such as tetrachlorosilane.

In all embodiments of this invention, whenever a reference is made to the "original double bond" or the "original unsaturation" of the block or random polymer (or copolymer), it is understood to mean the double bond(s) in the polymer prior to the hydrogenation reaction. By contrast, the terms "residual double bond(s)" and "residual unsaturation", as used herein, refer to the unsaturated group(s), typically excluding aromatic unsaturation, present in the copolymer after the selective hydrogenation reaction.

The molecular structure of the original or residual double bonds can be determined in any conventional manner, as is known to those skilled in the art, e.g., by infrared (IR) or nuclear magnetic resonance (NMR) analysis. In addition, the total original or residual unsaturation of the polymer can be quantified in any conventional manner, e.g., by reference to the Iodine Number of the polymer.

In any polymers of any of the embodiments of this invention, the microstructure of the polymerized conjugated diene of formula (3) must be such that the polymer is not excessively crystalline after the selective hydrogenation reaction. That is, after the selective hydrogenation reaction the polymer must retain its elastomeric properties, e.g., the polymer should contain not more than about 10% of polyethylene crystallinity. Generally, problems of crystallinity occur only when the polymer includes polymerized 1,3-butadiene. Limiting polymeric crystallinity may be accomplished in various ways. For example, this is accomplished by introducing side branches into the polymerized conjugated dienes of formula (1) and/or (3), e.g., by controlling the microstructure of 1,3-butadiene if it is the predominant monomer in the diene of formula (3); by using a mixture of dienes of formula (3) containing less than predominant amounts of 1,3-butadiene; or by using a single diene of formula (3), other than 1,3-butadiene. More particularly, if the conjugated diene(s) of formula (3) is predominantly (at least 50% by mole) 1,3-butadiene, the side branches are introduced into the polymer by insuring that the polymerized diene of formula (3) contains a sufficient amount of the 1,2-units to prevent the selectively hydrogenated polymer from being excessively crystalline. Thus, if the conjugated diene of formula (3) is predominantly (at least 50% by mole, e.g., 100% by mole) 1,3-butadiene, the polymerized diene of formula (3), prior to the selective hydrogenation reaction, must contain not more than about 75% wt., preferably from about 10% wt. to about 70% wt., and most preferably from about 35% wt. to about 55% wt. of the 1,4-units, and at least about 25% wt., preferably from about 30% wt. to about 90% wt., and most preferably from about 45% wt. to about 65% wt. of the 1,2-units. If the polymerized diene(s) of formula (3) contains less than 50% by mole of 1,3-butadiene, e.g., 1,3-pentadiene is used as the only diene of formula (3), the microstructure of the polymerized diene of formula (3) prior to the selective hydrogenation reaction is not critical since, after hydrogenation, the resulting polymer will contain substantially no crystallinity.

Homopolymers or mixtures of dienes of formula (1) or (3) may be used to prepare block copolymers $(I)_x$-$(B)_y$, or any of the random copolymers or star-branched block and random polymers of the invention. Similarly, mixtures of aryl-substituted olefins may also be used to prepare block, random, or star-branched copolymers of this invention. Accordingly, whenever a reference is made herein to a diene of formula (1) or (3), or to an aryl-substituted olefin, it may encompass more than one diene of formula (1) or (3), respectively, and more than one aryl-substituted olefin.

The block copolymers of this invention comprise two or more alternating blocks, identified above. Linear block copolymers having two blocks and block copolymers having three or more blocks are contemplated herein.

The block polymers useful according to the invention typically include at least one block which is substantially completely saturated, while also including at least one block containing controlled levels of unsaturation providing a hydrocarbon elastomer with selectively positioned unsaturation for subsequent functionalization. For the copolymers prepared from two different conjugated dienes, it has been found that the two dienes in the copolymers hydrogenate at different rates, permitting selective control of the placement of residual unsaturation.

The many variations in composition, molecular weight, molecular weight distribution, relative block lengths, microstructure, branching, and Tg (glass transition temperature) attainable with the use of anionic techniques employed in the preparation of our polymers will be obvious to those skilled in the art.

While not wishing to limit the molecular weight range of liquid elastomers prepared according to our invention, the minimum molecular weight for these liquid polymers is at least about 2,000, preferably above 3,000 to about 50,000, and most preferably about 5,000 to about 35,000. The star-branched block and random copolymers of this invention may have substantially higher molecular weights and still retain liquid properties.

All numerical values of molecular weight given in this specification and the drawings are of number average molecular weight (Mn).

The invention will be described hereinafter in terms of the embodiments thereof summarized above. However, it will be apparent to those skilled in the art, that the invention is not limited to these particular embodiments, but, rather, it covers all the embodiments encompassed by the broadest scope of the description of the invention.

Copolymers From at Least Two Dissimilar Conjugated Dienes

In this embodiment of the invention, there are provided copolymers of two dissimilar conjugated dienes, preferably isoprene and 1,3-butadiene. The two monomers can be polymerized by anionic polymerization process in either a block, tapered block, or random fashion.

The copolymers of this embodiment include a first conjugated diene having at least five (5) carbon atoms and the following formula:

(1)

wherein $R^1$–$R^6$ are each hydrogen or a hydrocarbyl group, provided that at least one of $R^1$–$R^6$ is a hydrocarbyl group, and further provided that, when polymerized, the structure of the double bond in the polymerized conjugated diene of formula (1) has the following formula:

(2)

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups. In the double bond of the polymerized conjugated diene of formula (2), $R^I$, $R^{II}$, $R^{III}$ and $R^{IV}$ may all be hydrocarbyl groups.

The polymers of this embodiment also include a second conjugated diene, different from the first conjugated diene, having at least four (4) carbon atoms and the following formula:

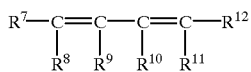

(3)

wherein $R^7$–$R^{12}$ are each hydrogen or a hydrocarbyl group, provided that the structure of the double bond in the polymerized conjugated diene of formula (3) has the following formula:

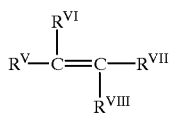

(4)

wherein $R^V$, $R^{VI}$, $R^{VII}$ and $R^{VIII}$ are each hydrogen (H) or a hydrocarbyl group, provided that one of $R^V$ or $R^{VI}$ is hydrogen, one of $R^{VII}$ or $R^{VIII}$ is hydrogen, and at least one of $R^V$, $R^{VI}$, $R^{VII}$ and $R^{VIII}$ is a hydrocarbyl group.

Following polymerization the diene copolymer of this embodiment is preferably functionalized by a method which includes selectively hydrogenating the copolymer to provide a selectively hydrogenated copolymer, followed by functionalizing the selectively hydrogenated copolymer to provide a functionalized copolymer having at least one polar functional group.

The polymers of this embodiment include a first conjugated diene of formula (1) in an amount of from about 0.5% wt. to about 30% wt., and a second conjugated diene in an amount of from about 70% wt. to about 99.5% wt. Preferably, a first conjugated diene is included in an amount of from about 1% wt. to about 25% wt., and a second conjugated diene in an amount of from about 75% to about 99% wt. More preferably, a first conjugated diene is included in an amount of from about 5% wt. to about 20% wt., and a second conjugated diene is included in an amount of from about 80% to about 95% wt.

The polymers of this embodiment include block copolymers having at least two alternating blocks:

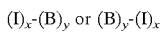

In this case, the polymer includes at least one block (I). The block (I) is a block of at least one polymerized conjugated diene of formula (1) as described above. These block copolymers also include at least one polymerized block (B). The block (B) is a block of at least one polymerized conjugated diene of formula (3) described above.

In the block copolymers of this embodiment, x is at least 1, preferably from about 1 to about 600, and most preferably from about 1 to about 350. The above definition of x means that each of the (I) blocks is polymerized from at least 1, preferably about 1–600, and more preferably about 1–350, monomer units.

In the block copolymers of this embodiment, y is at least 25, preferably from about 30 to about 4,000, more preferably from about 30 to about 2,800. The above definition of y means that each of the (B) blocks is polymerized from at least 25, preferably about 304,000, and more preferably about 30–2,800, monomer units.

The block copolymer comprises about 0.5 to about 25%, preferably about 1 to about 20% by wt. of the (1) blocks, and about 80 to about 99.5%, preferably about 80 to about 99% by wt. of the (B) blocks.

In any of the copolymers of this embodiment, the structures of the double bonds defined by formula (2) and (4) are necessary to produce copolymers which can be selectively hydrogenated in the manner described herein, to produce the selectively hydrogenated block and random copolymers of this invention.

The hydrocarbyl group or groups in the formula (1) and (2) are the same or different and they are substituted or unsubstituted alkyl, alkenyl, cycloalkyl, cycloalkenyl, aryl, alkaryl, or aralkyl groups, or any isomers thereof. Suitable hydrocarbyl groups are alkyls of 1–20 carbon atoms, alkenyls of 1–20 carbon atoms, cycloalkyls of 5–20 carbon atoms, aryls of 6–12 carbon atoms, alkaryls of 7–20 carbon atoms or aralkyls of 7–20 carbon atoms. Examples of suitable alkyl groups are methyl, ethyl, propyl, butyl, pentyl, hexyl, heptyl, octyl, decyl, methyl-decyl or dimethyl-decyl. Examples of suitable alkenyl groups are ethenyl, propenyl, butenyl, pentenyl or hexenyl. Examples of suitable cycloalkyl groups are cyclohexyl or methylcyclohexyl. Examples of suitable cycloalkenyl groups are 1-, 2-, or 3-cyclohexenyl or 4-methyl-2-cyclohexenyl. Examples of suitable aryl groups are phenyl or diphenyl. Examples of suitable alkaryl groups are 4-methyl-phenyl (p-tolyl) or p-ethyl-phenyl. Examples of suitable aralkyl groups are benzyl or phenethyl. Suitable conjugated dienes of formula (1) used to polymerize the (I) block are isoprene, 2,3-dimethyl-butadiene, 2-methyl-1,3-pentadiene, myrcene, 3-methyl-1,3-pentadiene, 4-methyl-1,3-pentadiene, 2-phenyl-1,3-butadiene, 2-phenyl-1,3-pentadiene, 3-phenyl-1,3 pentadiene, 2,3-dimethyl-1,3-pentadiene, 2-hexyl-1,3-butadiene, 3-methyl-1,3-hexadiene, 2-benzyl-1,3-butadiene, 2-p-tolyl-1,3-butadiene, or mixtures thereof, preferably isoprene, myrcene, 2,3-dimethyl-butadiene, or 2-methyl-1, 3-pentadiene, and most preferably isoprene.

The hydrocarbyl group or groups in the formula (3) may or may not be the same as those in formula (4). These hydrocarbyl groups are the same as those described above in conjunction with the discussion of the hydrocarbyl groups of formula (1) and (2). Suitable monomers for the (B) block are 1,3-butadiene, 1,3-pentadiene, 2,4-hexadiene, 1,3-hexadiene, 1,3-heptadiene, 2,4-heptadiene, 1,3-octadiene, 2,4-octadiene, 3,5-octadiene, 1,3-nonadiene, 2,4-nonadiene, 3,5-nonadiene, 1,3-decadiene, 2,4decadiene, 3,5-decadiene, or mixtures thereof, preferably 1,3-butadiene, 1,3-pentadiene, 2,4-hexadiene, or 1,3-hexadiene, and most preferably it is 1,3-butadiene. It is generally preferred that each of the (B) blocks is polymerized from a single monomer.

The scope of this embodiment, and of any other embodiments of the invention wherein the block (B) is used, also encompasses polymers wherein the block (B) may comprise copolymers of one or more conjugated diene of formula (3) and controlled amounts (about 0.3 to about 30 mole %) of an aryl-substituted olefin, e.g., styrene or other suitable monomers (such as alkylated styrene, vinyl naphthalene, or alkylated vinyl naphthalene) incorporated for control of glass transition temperature (Tg), density, solubility parameters and refractive index. Similarly, the scope of this embodiment also encompasses polymers wherein the block (B) may be comprised of copolymers of one or more conjugated diene of formula (3) and any other anionically polymerizable monomer capable of polymerizing with the conjugated diene of formula (3). Similar considerations also apply in the case of the (I) block(s), which can include similar styrene/diene copolymers.

The copolymer is polymerized by anionic polymerization, discussed in detail below. As will be apparent to those skilled in the art, the block copolymer of this embodiment contains at least two alternating blocks, (I)-(B) or (B)-(I), referred to herein as diblocks. The block copolymer of this embodiment may contain three alternating blocks, e.g., (I)-(B)-(I), referred to herein as triblocks or triblock units, but it may contain an unlimited number of blocks. The functionalization of any of these copolymers is conducted in a conventional manner and is described below.

After the (I)-(B) copolymer is polymerized, it is subjected to a selective hydrogenation reaction during which the polymerized conjugated dienes of formula (3) of the copolymer are selectively hydrogenated to such an extent that they contain substantially none of the original unsaturation, while the polymerized conjugated dienes of formula (1) of the copolymer retain a sufficient amount of their original unsaturation to permit functionalization.

Generally, for a copolymer wherein the conjugated dienes of formula (1) and (3) are polymerized to provide unsaturation of formula (2) and (4), respectively, as discussed above, the Iodine Number for the unsaturation of formula (2) after the selective hydrogenation reaction is from about 20% to about 100%, preferably from about 50% to about 100%, and most preferably about 100%, of the Iodine Number prior to the selective hydrogenation reaction; and for the unsaturation of formula (4) it is from about 0% to about 10%, preferably from about 0% to about 0.5%, and most preferably from about 0% to about 0.2%, of the Iodine Number prior to the selective hydrogenation reaction. The Iodine Number, as is known to those skilled in the art, is defined as the theoretical number of grams of iodine which will add to the unsaturation in 100 grams of olefin and is a quantitative measure of unsaturation.

In this embodiment of the invention, although the microstructure of the (I) blocks is not critical and may consist of 1,2-, 3,4- and/or 1,4-units, schematically represented below for the polyisoprene blocks, when a polar compound is used during the polymerization of the (I) block, the (I) blocks comprise primarily (at least about 50% wt.) 3,4-units, the rest being primarily (less than about 50% wt.) 1,4-units; when the polar compound is not used during the polymerization of the (I) block, the (I) blocks comprise primarily (about 80% wt.) 1,2-units, the rest being primarily 1,2- and 3,4-units.

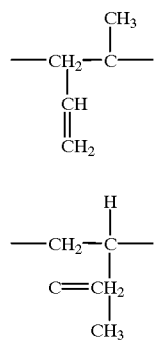

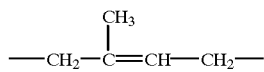

The microstructure of the (B) blocks, when the predominant monomer used to polymerize the (B) blocks is 1,3-butadiene, should be a mixture of 1,4- and 1,2- units schematically shown below for the polybutadiene blocks:

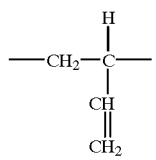

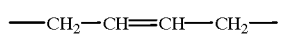

since the hydrogenation of the predominantly 1,4-microstructure produces a crystalline polyethylene segment. The microstructure of the (I) and (B) blocks (as well as of the polymerized conjugated dienes of formula (1) or (3) in any polymers of this invention) is controlled in a conventional manner, e.g., by controlling the amount and nature of the polar compounds used during the polymerization reaction, and the reaction temperature. In one particularly preferred embodiment, the (B) block contains about 50% of the 1,2- and about 50% of the 1,4- microstructure. If the (B) block is poly-1,3-butadiene, the hydrogenation of the (B) segment containing from about 50% to about 60% of the 1,2-microstructure content produces an elastomeric center block which is substantially an ethylene-butene-1 copolymer having substantially no crystallinity. If the (B) block is polymerized from 1,3-pentadiene, the microstructure is not critical.

The terms "1,2-", "1,4-", and "3,4-microstructure" or "units" as used in this application refer to the products of polymerization obtained by the 1,2-, 1,4- and 3,4-, respectively, mode of addition of monomer units.

We surprisingly discovered that the polymerized conjugated dienes of formula (3), e.g., the dienes employed in (B) blocks, of the polymers of this invention are selectively hydrogenated in our hydrogenation process much faster than the polymerized conjugated dienes of formula (1), e.g., the dienes used in the (I) blocks. This is not evident from the teachings of Falk, discussed above, because Falk teaches that double bonds of the di-substituted 1,4-polybutadiene units are hydrogenated selectively in the presence of double bonds of the tri-substituted 1,4-polyisoprene units (which hydrogenate very slowly). We surprisingly discovered that the di-substituted double bonds of the 1,4-polybutadiene units are hydrogenated along with the monosubstituted double bonds of the 1,2-polybutadiene units, while the di-substituted double bonds of the 3,4-polyisoprene units are hydrogenated at a much slower rate than the aforementioned polybutadienes. Thus, in view of Falk's disclosure it is surprising that the di-substituted double bonds of the 1,4-polybutadiene units are hydrogenated selectively in the presence of the di-substituted double bonds of the 3,4-polyisoprene units. This is also surprising in view of the teachings of Hoxmeier, Published European Pat. No. Application, Publication No. 0 315 280, who discloses that the di-substituted double bonds of the 1,4-polybutadiene units, monosubstituted double bonds of the 1,2- polybutadiene units and di-substituted double bonds of the 3,4-polyisoprene units are hydrogenated simultaneously at substantially the same rates. For example, for the block copolymers of this invention, wherein the (1) block is polyisoprene and the (B) block is polybutadiene, Fourier Transform Infrared (FTIR) analysis of selectively hydrogenated block copolymers of the invention, such as I-B-I triblock polymers, indicates that the hydrogenation of the double bonds of the 1,2-polybutadiene units proceeds most rapidly, followed by the hydrogenation of the double bonds of the 1,4-polybutadiene units. Infrared absorptions caused by these groups disappear prior to appreciable hydrogenation of the polyisoprene units.

Accordingly, by controlling the amount and placement of 1,2-versus 1,4-microstructure, as well as the amount and placement of polyisoprene units, it is now possible to control the amount and placement of unsaturation remaining in the polymers after hydrogenation.

After the block copolymer is prepared, it is subjected to a selective hydrogenation reaction to hydrogenate primarily the (B) block(s). The selective hydrogenation reaction and the catalyst are described in detail below. After the hydrogenation reaction is completed, the selective hydrogenation catalyst is removed from the block copolymer, and the polymer is isolated by conventional procedures, e.g., alcohol flocculation, steam stripping of solvent, or non-aqueous solvent evaporation. An antioxidant, e.g., vitamin E, is normally added to the polymer solution prior to polymer isolation.

Random Copolymers

Random copolymers of this invention have controlled amounts of unsaturation incorporated randomly in an otherwise saturated backbone. In contrast to EPDM, the level of unsaturation can be easily controlled, e.g., to produce polymers having Iodine Number of from about 5 to about 100, to provide a wide variation in the degree of functionalization.

In one embodiment, the random copolymers are polymerized from the same monomers used to polymerize the block copolymers $(I)_x$-$(B)_y$, described elsewhere herein. In particular, the random copolymers may be made by polymerizing at least one conjugated diene of formula (1) with at least one conjugated diene of formula (3), both defined above. This random copolymer contains from about 1.0% to about 40%, preferably from about 1.0% to about 20%, by mole of the polymerized conjugated diene of formula (1) and from about 60% to about 99%, preferably from about 80% to about 99% by mole of the polymerized conjugated diene of formula (3). Suitable conjugated dienes of formula (1) are exemplified above. The most preferred conjugated diene of formula (1) for the copolymerization of these random copolymers is isoprene. Suitable conjugated dienes of formula (3) are also exemplified above. 1,3-butadiene is the most preferred conjugated diene of formula (3) for the polymerization of the random copolymer of this embodiment. Thus, most preferably, in this embodiment, the random copolymer is polymerized from isoprene and 1,3-butadiene, and it contains from about 1% wt. to about 20% wt. of the isoprene units and from about 80% wt. to about 99% wt. of the butadiene units. The isoprene units have primarily (i.e., from about 50% wt. to about 90% wt.) the 3,4-microstructure.

The random copolymers are subjected to the selective hydrogenation reaction discussed above for the block copolymers, during which polymerized conjugated diene units of formula (3) are substantially completely hydrogenated, while the conjugated diene units of formula (1) are hydrogenated to a substantially lesser extent, i.e., to such an extent that they retain a sufficient amount of their original unsaturation to functionalize the copolymer, thereby producing polymers having random unsaturation proportional to the unsaturation in the polymerized dienes of formula (1). For example, for random copolymer polymerized from a diene of formula (1) and a different diene of formula (3), the Iodine Number before selective hydrogenation for the polymer is about 450. After selective hydrogenation, the Iodine Number for the polymer is from about 10 to about 50, with most of the unsaturation being contributed by the diene of formula (1).

Star-Branched Polymers

The invention is also directed to star-branched block and random polymers. The star-branched block polymers are made from any combination of blocks (I) and (B), defined above.

The star-branched (I)-(B) block polymers comprise from about 0.5% wt. to about 25% wt., preferably from about 1% wt. to about 20% wt., of the (I) blocks, and from about 75% wt. to about 99.5% wt., preferably from about 80% wt. to about 99% wt., of the (B) blocks.

The star-branched block polymers are selectively hydrogenated in the selective hydrogenation process of this invention to such an extent that blocks (B) contain substantially none of the original unsaturation, while each of the blocks (I) respectively, retains a sufficient amount of the original unsaturation of the conjugated dienes present in these blocks to functionalize the star-branched block polymers. Thus, for the I-(B) star-branched block polymer, after the selective hydrogenation reaction, the Iodine Number for the (I) blocks is from about 10% to about 100%, preferably from about 25% to about 100%, more preferably from about 50% to about 100%, and most preferably about 100%, of the Iodine Number prior to the selective hydrogenation reaction; and for the (B) blocks it is from about 0% to about 10%, preferably from about 0% to about 0.5%, of the Iodine Number prior to the selective hydrogenation reaction.

The star-branched random polymers are made from any combination of at least one diene of formula (1) and at least one diene of formula (3), different from the diene of formula (1), or from any combination of at least one aryl-substituted olefin and at least one diene of formula (1) or (3), all of which are the same as those discussed above. The star-branched random polymers of the dienes of formula (1) and (3), which must be different from each other, comprise from about 0.5% wt. to about 25% wt., preferably from about 1% wt. to about 20% wt., of the diene of formula (1), and from about 75% wt. to about 99.5% wt., preferably from about 80% wt. to about 99% wt., of the diene of formula (3). The star-branched random polymers of the aryl-substituted olefin and the diene of formula (1) or (3) comprise from about 0.5% wt. to about 50% wt., preferably from about 1% wt. to about 25% wt., of the aryl-substituted olefin, and from about 50% wt. to about 99.5% wt., preferably from about 75% wt. to about 99% wt., of the diene of formula (1) or (3).

The star-branched random diene polymers are also selectively hydrogenated in the selective hydrogenation process of this invention to such an extent that the polymerized dienes of formula (3) contain substantially none of the original unsaturation, while the polymerized dienes of formula (1) retain a sufficient amount of the original unsaturation to functionalize the star-branched random polymers. Thus, for the star-branched random polymer of the conjugated diene of formula (1) and a different diene of formula (3), both identified above, the Iodine Number for the polymerized diene of formula (1), after the selective hydrogenation reaction, is from about 10% to about 100%, preferably from about 25% to about 100%, more preferably from about 50% to about 100%, and most preferably about 100%, of the Iodine Number prior to the selective hydrogenation reaction; and for the polymerized diene of formula (3) it is from about 0% to about 10%, preferably from about 0% to about 0.5%, of the Iodine Number prior to the selective hydrogenation reaction.

Polymerization Reaction

The polymers of this invention are polymerized by any known polymerization processes, preferably by an anionic polymerization process. Anionic polymerization is well known in the art and it is utilized in the production of a variety of commercial polymers. An excellent comprehensive review of the anionic polymerization processes appears in the text *Advances in Polymer Science 56, Anionic Polymerization,* pp. 1–90, Springer-Verlag, Berlin, Heidelberg, New York, Tokyo 1984 in a monograph entitled Anionic Polymerization of Non-polar Monomers Involving Lithium, by R. N. Young, R. P. Quirk and L. J. Fetters, incorporated herein by reference. The anionic polymerization process is conducted in the presence of a suitable anionic catalyst (also known as an initiator), such as n-butyl-lithium, sec-butyl-lithium, t-butyl-lithium, sodium naphthalide or, cumyl potassium. The amount of the catalyst and the amount of the monomer in the polymerization reaction dictate the molecular weight of the polymer. The polymerization reaction is conducted in solution using an inert solvent as the polymerization medium, e.g., aliphatic hydrocarbons, such as hexane, cyclohexane, or heptane, or aromatic solvents, such as benzene or toluene. In certain instances, inert polar solvents, such as tetrahydrofuran, can be used alone as a solvent, or in a mixture with a hydrocarbon solvent.

The polymerization process will be exemplified below for the polymerization of one of the embodiments of the invention, e.g., a triblock of polyisoprene-polybutadiene-polyisoprene. However, it will be apparent to those skilled in the art that the same process principles can be used for the polymerization of all polymers of the invention.

The process, when using a lithium-based catalyst, comprises forming a solution of the isoprene monomer in an inert hydrocarbon solvent, such as cyclohexane, modified by the presence therein of one or more polar compounds selected from the group consisting of ethers, thioethers, and tertiary amines, e.g., tetrahydrofuran. The polar compounds are necessary to control the microstructure of the butadiene center block, i.e., the content of the 1,2-structure thereof. The higher the content of the polar compounds, the higher will be the content of the 1,2-structure in these blocks. Since the presence of the polar compound is not essential in the formation of the first polymer block with many initiators unless a high 3,4-structure content of the first block is desired, it is not necessary to introduce the polar compound at this stage, since it may be introduced just prior to or together with the addition of the butadiene in the second polymerization stage. Examples of polar compounds which may be used are dimethyl ether, diethyl ether, ethyl methyl ether, ethyl propyl ether, dioxane, diphenyl ether, dipropyl ether, tripropyl amine, tributyl amine, trimethyl amine, triethyl amine, and N-N-N'-N'-tetramethyl ethylene diamine. Mixtures of the polar compounds may also be used. The amount of the polar compound depends on the type of the polar compound and the polymerization conditions as will be apparent to those skilled in the art. The effect of polar compounds on the polybutadiene microstructure is detailed in Antkowiak et al. The polar compounds also accelerate the rate of polymerization. If monomers other than 1,3-butadiene, e.g., pentadiene, are used to polymerize the central blocks (B), polar compounds are not necessary to control the microstructure because such monomers will inherently produce polymers which do not possess crystallinity after hydrogenation.

When the alkyl lithium-based initiator, a polar compound and an isoprene monomer are combined in an inert solvent, polymerization of the isoprene proceeds to produce the first terminal block whose molecular weight is determined by the ratio of the isoprene to the initiator. The living polyisoprenyl anion formed in this first step is utilized as the catalyst for further polymerization. At this time, butadiene monomer is introduced into the system and block polymerization of the second block proceeds, the presence of the polar compound now influencing the desired degree of branching (1,2-structure) in the polybutadiene block. The resulting product is a living diblock polymer having a terminal anion and a lithium counterion. The living diblock polymer serves as a catalyst for the growth of the final isoprene block, formed when isoprene monomer is again added to the reaction vessel to produce the final polymer block, resulting in the formation of the I-B-I triblock. Upon completion of polymerization, the living anion, now present at the terminus of the triblock, is destroyed by the addition of a proton donor, such as methyl alcohol or acetic acid. The polymerization reaction is usually conducted at a temperature of between about 0° C. and about 100° C., although higher temperatures can be used. Control of a chosen reaction temperature is desirable since it can influence the effectiveness of the polar compound additive in controlling the polymer microstructure. The reaction temperature can be, for example, from about 50° C. to about 80° C. The reaction pressure is not critical and varies from about atmospheric to about 100 psig.

If the polar compounds are utilized prior to the polymerization of the first (I) segment, (I) blocks with high 3,4-unit content are formed. If polar compounds are added after the initial (I) segment is prepared, the first (I) segment will possess a high percentage of 1,4-microstructure (which is tri-substituted), and the second (I) segment will have a high percentage of 3,4-microstructure.

The production of triblock polymers having a high 1,4-unit content on both of the terminal (I) blocks is also possible by the use of coupling techniques illustrated below for a polyisoprene-polybutadiene-polyisoprene block copolymer:

RLi
ISOPRENE→1,4-POLYISOPRENE
POLAR COMPOUND →1,4-POLYISOPRENE-POLYBUTADIENE
BUTADIENE
COUPLING AGENT 1,4-POLYISOPRENE-POLYBUTADIENE-1,4-POLYISOPRENE →

The substitution of myrcene for the isoprene during the polymerization of the (I) blocks insures the incorporation of a high proportion of tri-substituted double bonds, even in the presence of polar compounds since myrcene contains a pendant tri-substituted double bond which is not involved in the polymerization process. In a coupling process, similar to that described above, block polymers containing polyisoprene end blocks (or any other polymerized monomer suitable for use in the (I) block) having a high 3,4- microstructure content can be obtained by adding the polar compound prior to the isoprene (or another monomer) polymerization.

The use of the coupling technique for the production of triblock polymers reduces the reaction time necessary for the completion of polymerization, as compared to sequential addition of isoprene, followed by butadiene, followed by isoprene. Such coupling techniques are well known and utilize coupling agents such as esters, $CO_2$, iodine, dihaloalkanes, silicon tetrachloride, divinyl benzene, alkyl trichlorosilanes and dialkyl dichlorosilanes. The use of tri- or tetra-functional coupling agents, such as alkyl trichlorosilanes or silicon tetrachloride, permits the formation of macromolecules having 1- or 2- main chain branches, respectively. The addition of divinyl benzene as a coupling agent has been documented to produce molecules having up to 20 or more separately joined segments.

The use of some of the coupling agents provides a convenient means of producing star-branched block and random polymers. The star-branched block polymers are made from any combination of blocks (I) and (B), defined above. The star-branched random polymers are made from any combination of at least one diene of formula (1) and at least one diene of formula (3), different from the diene of formula (1), or from at least one aryl-substituted olefin, at least one diene of formula (1) and at least one diene of formula (3), different from the diene of formula (1). The molecular weight of the star-branched block and random copolymers will depend on the number of branches in each such copolymer, as will be apparent to those skilled in the art. Suitable coupling agents and reactions are disclosed in the following references which are incorporated herein by reference: U.S. Pat. No. Nos. 3,949,020; 3,594,452; 3,598,887; 3,465,065; 3,078,254; 3,766,301; 3,632,682; 3,668,279; and Great Britain patent Nos. 1,014,999; 1,074,276; 1,121,978.

Hydrogenation

Following polymerization, the polymers may be selectively hydrogenated, partially hydrogenated or completely hydrogenated. Selective hydrogenation of the polymer may be accomplished using techniques similar to those known in the art. A preferred method and catalyst are described in U.S. Pat. No. No. 5,187,236, the disclosure of which is incorporated herein by reference. The procedure and catalyst are described in greater detail below. In general, however, the previously described polymers can be contacted with hydrogen and a hydrogenation catalyst synthesized from a transition metal compound, typically nickel or cobalt, and an organometallic reducing agent, e.g., triethylaluminum. The hydrogenation proceeds at temperatures typically not in excess of about 40° C. and at pressures of from about 30 psi to about 200 psi. Generally, the polymers are hydrogenated such that substantially all of the unsaturation in formula (4) is removed, while much of that from formula (2) is retained.

The selective hydrogenation reaction will also be described below using a triblock of polyisoprene-polybutadiene-polyisoprene as an example. However, it will be apparent to those skilled in the art that any polymers of this invention can be selectively hydrogenated in the same manner.

In Example II below, the block copolymer is selectively hydrogenated to saturate the middle (polybutadiene) block. The method of selectively hydrogenating the polybutadiene block is similar to that of Falk, *Coordination Catalysts for the Selective Hydrogenation of Polymeric Unsaturation*, Journal of Polymer Science: Part A-1, 9:2617–23 (1971), but it is conducted with a novel hydrogenation catalyst and process used herein. Any other known selective hydrogenation methods may also be used, as will be apparent to those skilled in the art, but it is preferred to use the method described herein. In summary, the selective hydrogenation method preferably used herein comprises contacting the previously-prepared block copolymer with hydrogen in the presence of the novel catalyst composition.

The novel hydrogenation catalyst composition and hydrogenation process are described in detail in previously cited application Ser. No. 07/466,136. The hydrogenation catalyst composition is synthesized from at least one transition metal compound and an organometallic reducing agent. Suitable transition metal compounds are compounds of metals of Group IVb, Vb, VIb or VIII, preferably IVb or VIII of the Periodic Table of the Elements, published in *Lange's Handbook of Chemistry*, 13th Ed., McGraw-Hill Book Company, New York (1985) (John A. Dean, ed.). Non-limiting examples of such compounds are metal halides, e.g., titanium tetrachloride, vanadium tetrachloride; vanadium oxytrichloride, titanium and vanadium alkoxides, wherein the alkoxide moiety has a branched or unbranched alkyl radical of 1 to about 20 carbon atoms, preferably I to about 6 carbon atoms. Preferred transition metal compounds are metal carboxylates or alkoxides of Group IVb or VIII of the Periodic Table of the Elements, such as nickel (II) 2-ethylhexanoate, titanium isopropoxide, cobalt (II) octoate, nickel (II) phenoxide and ferric acetylacetonate.

The organometallic reducing agent is any one or a combination of any of the materials commonly employed to activate Ziegler-Natta olefin polymerization catalyst components containing at least one compound of the elements of Groups Ia, IIa, IIb, IIIa, or IVa of the Periodic Table of the Elements. Examples of such reducing agents are metal alkyls, metal hydrides, alkyl metal hydrides, alkyl metal halides, and alkyl metal alkoxides, such as alkyllithium compounds, dialkylzinc compounds, trialkylboron compounds, trialkylaliminum compounds, alkylaluminum halides and hydrides, and tetraalkylgermanium compounds. Mixtures of the reducing agents may also be employed. Specific examples of useful reducing agents include n-butyllithium, diethylzinc, di-n-propylzinc, triethylboron, diethylaluminumethoxide, triethylaluminum, trimethylaluminum, triisobutylaluminum, tri-n-hexylaluminum, ethylaluminum dichloride, dibromide, and dihydride, isobutyl aluminum dichloride, dibromide, and dihydride, diethylaluminum chloride, bromide, and hydride, di-n-propylaluminum chloride, bromide, and hydride, diisobutylaluminum chloride, bromide and hydride, tetramethylgermanium, and tetraethylgermanium. Organometallic reducing agents which are preferred are Group IIIa metal alkyls and dialkyl metal halides having 1 to about 20 carbon atoms per alkyl radical. More preferably, the reducing agent is a trialkylaluminum compound having 1 to about 6 carbon atoms per alkyl radical. Other reducing agents which can be used herein are disclosed in Stevens et al., U.S. Pat. No. 3,787,384, column 4, line 45 to column 5, line 12 and in Strobel et al., U.S. Pat. No. 4,148,754, column 4, line 56 to column 5, line 59, the entire contents of both of which are incorporated herein by reference. Particularly preferred reducing agents are metal alkyl or hydride derivatives of a metal selected from Groups Ia, IIa and IIIa of the Periodic Table of the Elements, such as n-butyl lithium, sec-butyl lithium, n-hexyl lithium, phenyl-lithium, triethylaluminum, tri-isobutylaluminum, trimethyl-aluminum, diethylaluminum hydride and dibutylmagnesium.

The molar ratio of the metal derived from the reducing agent to the metal derived from the transition metal compound will vary for the selected combinations of the reducing agent and the transition metal compound, but in general it is about 1:1 to about 12:1, preferably about 1.5:1 to about 8:1, more preferably about 2:1 to about 7:1, and most preferably about 2.5:1 to about 6:1. it will be apparent to those skilled in the art that the optimal ratios will vary depending upon the transition metal and the organometallic agent used, e.g., for the trialkylaluminum/nickel(II) systems, the preferred aluminum: nickel molar ratio is about 2.5:1 to about 4:1, for the trialkylaluminum/cobalt(II) systems, the preferred aluminum:cobalt molar ratio is about 3:1 to about 4:1, and for the trialkylaluminum/titanium(IV) alkoxides systems, the preferred aluminum: titanium molar ratio is about 3:1 to about 6:1.

The mode of addition and the ratio of the reducing agent to the transition metal compound are important in the production of the novel hydrogenation catalyst having superior selectivity, efficiency and stability, as compared to prior art catalytic systems. During the synthesis of the catalysts it is preferred to maintain the molar ratio of the reactants used to synthesize the catalyst substantially constant. This can be done either by the addition of the reducing agent, as rapidly as possible, to a solution of the transition metal compound, or by a substantially simultaneous addition of the separate streams of the reducing agent and the transition metal compound to a catalyst synthesis vessel in such a manner that the selected molar ratios of the metal of the reducing agent to the metal of the transition metal compound are maintained substantially constant throughout substantially the entire time of addition of the two compounds. The time required for the addition must be such that excessive pressure and heat build-up are avoided, i.e., the temperature should not exceed about 80° C. and the pressure should not exceed the safe pressure limit of the catalyst synthesis vessel.

In a preferred embodiment, the reducing agent and the transition metal compound are added substantially simultaneously to the catalyst synthesis vessel in such a manner that the selected molar ratio of the reducing agent to the transition metal compound is maintained substantially constant during substantially the entire time of the addition of the two compounds. This preferred embodiment permits the control of the exothermic reaction so that the heat build-up is not excessive, and the rate of gas production during the catalyst synthesis is also non excessive—accordingly, the gas build-up is relatively slow. In this embodiment, carried out with or without a solvent diluent, the rate of addition of the catalyst components is adjusted to maintain the synthesis reaction temperature at or below about 80° C., which promotes the formation of the selective hydrogenation catalyst. Furthermore, the selected molar ratios of the metal of the reducing agent to the metal of the transition metal compound are maintained substantially constant throughout the entire duration of the catalyst preparation when the simultaneous mixing technique of this embodiment is employed.

In another embodiment, the catalyst is formed by the addition of the reducing agent to the transition metal compound. In this embodiment, the timing and the order of addition of the two reactants is important to obtain the hydrogenation catalyst having superior selectivity, efficiency and stability. Thus, in this embodiment, it is important to add the reducing agent to the transition metal compound in that order in as short a time period as practically possible. In this embodiment, the time allotted for the addition of the reducing agent to the transition metal compound is critical for the production of the novel catalyst. The term "as short a time period as practically possible" means that the time of addition is as rapid as possible, such that the reaction temperature is not higher than about 80° C. and the reaction pressure does not exceed the safe pressure limit of the catalyst synthesis vessel. As will be apparent to those skilled in the art, that time will vary for each synthesis and will depend on such factors as the types of the reducing agents, the transition metal compounds and the solvents used in the synthesis, as well as the relative amounts thereof, and the type of the catalyst synthesis vessel used. For purposes of illustration, a solution of about 15 mL of triethylaluminum in hexane should be added to a solution of nickel(II) octoate in mineral spirits in about 10–30 seconds. Generally, the addition of the reducing agent to the transition metal compound should be carried out in about 5 seconds (sec) to about 5 minutes (min), depending on the quantities of the reagents used. If the time period during which the reducing agent is added to the transition metal compound is prolonged, e.g., more than 15 minutes, the synthesized catalyst is less selective, less stable, and may be heterogeneous.

In the embodiment wherein the reducing agent is added as rapidly as possible to the transition metal compound, it is also important to add the reducing agent to the transition metal compound in the aforementioned sequence to obtain the novel catalyst. The reversal of the addition sequence, i.e., the addition of the transition metal compound to the reducing agent, or the respective solutions thereof, is detrimental to the stability, selectivity, activity, and homogeneity of the catalyst and is, therefore, undesirable.

In all embodiments of the hydrogenation catalyst synthesis, it is preferred to use solutions of the reducing agent and the transition metal compound in suitable solvents, such as hydrocarbon solvents, e.g., cyclohexane, hexane, pentane, heptane, benzene, toluene, or mineral oils. The solvents used to prepare the solutions of the reducing agent and of the transition metal compound may be the same or different, but if they are different, they must be compatible with each other so that the solutions of the reducing agent and the transition metal compound are fully soluble in each other.

The hydrogenation process comprises contacting the unsaturated polymer to be hydrogenated with an amount of the catalyst solution containing about 0.1 to about 0.5, preferably about 0.2 to about 0.3 mole percent of the transition metal based on moles of the polymer unsaturation. The hydrogen partial pressure is generally from about 5 psig to about several hundred psig, but preferably it is from about 10 psig to about 100 psig. The temperature of the hydrogenation reaction mixture is generally from about 0° C. to about 150° C., preferably from about 25° C. to about 80° C., more preferably from about 30° C. to about 60° C., since higher temperatures may lead to catalyst deactivation. The length of the hydrogenation reaction may be as short as 30 minutes and, as will be apparent to those skilled in the art, depends to a great extent on the actual reaction conditions employed. The hydrogenation process may be monitored by any conventional means, e.g., infra-red spectroscopy, hydrogen flow rate, total hydrogen consumption, or any combination thereof.

Upon completion of the hydrogenation process, unreacted hydrogen is either vented or consumed by the introduction of the appropriate amount of an unsaturated material, such as 1-hexene, which is converted to an inert hydrocarbon, e.g., hexane. Subsequently, the catalyst is removed from the resulting polymer solution by any suitable means, selected depending on the particular process and polymer. For a low molecular weight material, for example, catalyst residue removal may consist of a treatment of the solution with an oxidant, such as air, and subsequent treatment with ammonia and optionally methanol in amounts equal to the molar amount of the metals (i.e., the sum of the transition metal and the metal of the reducing agent) present in the hydrogenation catalyst to yield the catalyst residues as a filterable precipitate, which is filtered off. The solvent may then be removed by any conventional methods, such as vacuum stripping, to yield the product polymer as a clear, colorless fluid.

Alternatively, and in a preferred embodiment, upon completion of the hydrogenation reaction, the mixture is treated with ammonia in the molar amount about equal to that of the metals (i.e., the sum of the transition metal and the metal of the reducing agent) and aqueous hydrogen peroxide, in the molar amount equal to about one half to about one, preferably one half, of the amount of the metals. Other levels of the ammonia and peroxide are also operative, but those specified above are particularly preferred. In this method, a precipitate forms, which may be filtered off as described above.

In yet another alternative method, the catalyst may be removed by extraction with an aqueous mineral acid, such as sulfuric, phosphoric, or hydrochloric acid, followed by washing with distilled water. A small amount of a material commonly used as an aid in removing transition metal-based catalysts, such as a commercially available high molecular weight diamine, e.g., Jeffamine D-2000 from Huntsman, may be added to aid in phase separation and catalyst removal during the extractions. The resultant polymer solution is then dried over a drying agent, such as magnesium sulfate, separated from the drying agent and the solvent is then separated by any conventional methods, such as vacuum stripping, to yield a polymer as a clear fluid. Other methods of polymer isolation, such as steam or alcohol flocculation, may be employed depending upon the hydrogenated polymer properties.

After hydrogenation and purification is complete, the polymer can be formulated into a sunscreen.

Sunscreen Formulations

The sunscreen composition comprises from about 0.5 to about 10 wt. % of the polymer of the present invention; about 1 to about 15 wt. % of an ultraviolet sunscreening agent; about 1–5 wt. % of an emulsifier; about 0.1 to about 5 wt. % of a secondary waterproofing agent; about 0.5 to about 2 wt. % of a germicide and about 0.1 to about 0.5 wt. % of a fragrance. The remainder of the sunscreen composition is water, generally in an amount in the range of from about 50 to about 95 wt. %

The sunscreen formulations of the present invention are in the form of readily flowable liquids such as sprays, i.e. both aerosol and non-aerosol, paints and dips are advantageous for ease of application. However, the water resistance will be enhanced by formulating it for use as a paste, ointment, salve, gel or cream, which would dry quickly to leave water resistant or waterproof film on the skin.

Alcoholic systems, aqueous emulsions and anhydrous systems are contemplated for use in the present invention.

Effective amounts may vary depending on frequency of application and/or contact with moisture the formulations are typically used by applying from 0.1 to about 20 microliters per square centimeters of same for the skin of a subject and allowing it to dry. Reapplication can be made from one to several times per day, with the total number of applications being from about 1 to about 8 times.

EXAMPLES

The following examples are intended to assist in a further understanding of the invention. The particular materials and conditions employed are intended to be further illustrative of the invention and are not limiting upon the reasonable scope thereof.

In all of the following examples, the experimental polymerization and functionalization work was performed with dried reactors and equipment and under strictly anaerobic conditions. All % are % by weight. Extreme care must be used to exclude air, moisture and other impurities capable of interfering with the delicate chemical balance involved in the synthesis of the polymers of this invention, as will be apparent to those skilled in the art.

Example I

Preparation of Polymer Precursor Backbones

Using the procedure described in Example VII of U.S. Pat. No. 5,633,415, incorporated herein by reference, an isoprene-butadiene diblock polymer having a number average molecular weight of about 15,000 is prepared.

Example II

Selective Hydrogenation of the Polymer of Example I

The polymer solution of Example I is subjected to a selective hydrogenation procedure using a catalyst prepared by diethylaluminum ethoxide and cobalt octoate (3.5 to 1 molar ratio) and following general procedures as described in Example VIII of U.S. Pat. No. 5,633,415, incorporated herein by reference. The extent of hydrogenation is followed by Fourier Transfer Infrared (FTIR) and is continued until no absorption remains at 910 $cm^{-1}$ and 990 $cm^{-1}$(-1,2 polybutadiene structure) and essentially no residual trans double bonds are present as seen by disappearance of the 968 cm-1 absorption. The FTIR analysis of the polymers at the end of the selective hydrogenation typically indicates 0 to 10 trans polybutadiene double bonds and 50 to 100 vinylidene (-3,4 polyisoprene) double bonds remain— normalized to 100,000 molecular weight polymer chain. The polymer of Example I has 0 to 1.5 trans double bonds and 7.5 to 15 vinylidene double bonds (for subsequent functionalization).

The hydrogenation catalyst is removed by washing, as described in U.S. Pat. No. 5,633,415, or by a filtration procedure preceded by precipitation of the catalyst with essentially stoichiometric levels of acetic acid and hydrogen peroxide. After catalyst removal, the solvent is removed under reduced pressure to give the polymer.

Example III

Sunscreen Formulation Containing the Polymer of Example II

The following sunscreen formulation is prepared using the IB copolymer of Example II:

| Ingredient | Wt % |
|---|---|
| Deionized Water | 53.1 |
| Carbopol 940 (2% Solution) (thickener) | 7.5 |
| Pemelen TR-2 (2% Solution) | 7.5 |
| Na2EDTA | 0.1 |
| Hexylene Glycol | 2.0 |

-continued

| Ingredient | Wt % |
|---|---|
| Octyl Methoxycinnamate (sunscreen agent) | 7.5 |
| Oxybenzone (sunscreen agent) | 4.0 |
| Avobenzone (Parsol 1789) | 3.0 |
| IB Copolymer of Example II | 5.0 |
| Synthetic Ester | 5.0 |
| Dimethicone SF 96-350 | 1.0 |
| Amphisol | 2.0 |
| Arlacel 165 | 0.5 |
| Cetearyl Alcohol | 0.4 |
| Triethanolamine 99% | 0.15 |
| Phenonip | 1.0 |
| Fragrance Intarome 46515 | 0.25 |

Deionized Water, Carbopol 940 (2% Solution), Pemelen TR-2 (2% Solution), Na2EDTA, and Hexylene Glycol are heated to 75° C. with stirring to form a mixture. Octyl Methoxycinnamate (sunscreen agent), Oxybenzone (sunscreen agent), Avobenzone (Parsol 1789), IB Copolymer of Example II, Synthetic Ester, Dimethicone SF 96-350, Amphisol, Arlacel 165, and Cetearyl Alcohol are heated to 95° C. with stirring and added to the first mixture while maintaining stirring. The mixture is cooled to 40° C. and Triethanolamine 99%, Phenonip, and Fragrance Intarome 46515 are added to the mixture while stirring. The resultant is a spreadable, tack-free emulsion.

Water wash off performance is examined by applying the emulsion of Example III to human skin to a thickness of 0.5 mm. Conductance readings are taken before and after application. Water resistance is determined by increases in measured skin moisture content. The result is shown below in Table I.

Example IV

Comparative Sunscreen Formulation

A comparative sunscreen formulation is prepared in accordance with Example III. Performa™ (5 wt. %), an alphaolefin-isopropyl maleate-maleic anhydride copolymer is substituted for the IB copolymer (5 wt. %) of Example III. Water wash off performance is measured in accordance with Example III. The results are shown below in Table I.

Example V

Comparative Sunscreen Formulation

A comparative sunscreen formulation is prepared in accordance with Example III. Polyalphaolefin (3%) and Synthetic Ester (7%) are substituted for the IB copolymer (5%) and Synthetic Ester (5%) of Example III. Water wash off is measured in accordance with Example III. The results and shown below in Table I.

Example VI

Comparative Sunscreen Formulation

A comparative sunscreen formulation is prepared in accordance with Example III. Polyalphaolefin (5 wt. %) is substituted for the IB copolymer (5 wt %) of Example III. Water wash off is measured in accordance with Example III. The results are shown below in Table I.

TABLE I

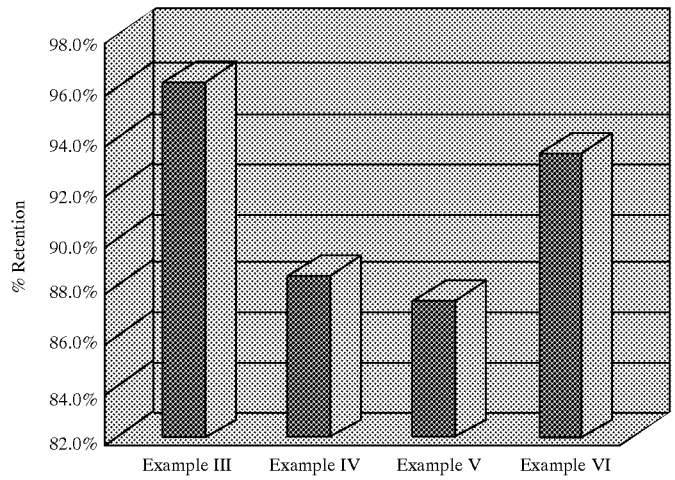

It will be apparent to those skilled in the art that the specific embodiments discussed above can be successfully repeated with ingredients equivalent to those generically or specifically set forth above and under variable process conditions. From the foregoing specification, one skilled in the art can readily ascertain the essential features of this invention and without departing from the spirit and scope thereof can adapt it to various diverse applications.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

What is claimed is:

1. A sunscreen composition having water resistance properties comprising a polymer and/or copolymer selected from the group consisting of isoprene, butadiene and/or styrene; water and a sunscreen agent.

2. The sunscreen composition according to claim 1 wherein said polymer and/or copolymer is in an amount in the range of from about 0.5 to about 10 wt. % based on the total weight of the sunscreen composition.

3. The sunscreen composition of claim 1 wherein said polymer and/or copolymer is selectively hydrogenated to provide a selectively hydrogenated polymer and/or copolymer.

4. A sunscreen composition having water resistant properties comprising a copolymer of a first conjugated diene and a second conjugated diene, wherein:

said first conjugated diene comprises at least one relatively more substituted conjugated diene having at least five carbon atoms and the formula:

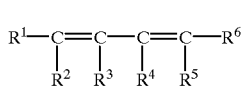
(1)

wherein $R^1$–$R^6$ are each hydrogen or a hydrocarbyl group, provided that at least one of $R^1$–$R^6$ is a hydrocarbyl group, provided that after polymerization, the unsaturation of the polymerized conjugated diene of formula (1) has the formula:

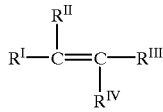
(2)

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups; and said second conjugated diene comprises at least one relatively less substituted conjugated diene different from the first conjugated diene and having at least four carbon atoms and the formula:

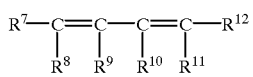
(3)

wherein $R^7$–$R^{12}$ are each hydrogen or a hydrocarbyl group, provided that after polymerization, the unsaturation of the polymerized conjugated diene of formula (3) has the formula:

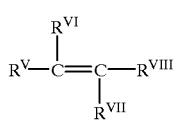
(4)

wherein $R^V$, $R^{VI}$, $R^{VII}$ and $R^{VIII}$ are each hydrogen or a hydrocarbyl group, provided that one of $R^V$ or $R^{VI}$ is hydrogen, one of $R^{VII}$ or $R^{VIII}$ is hydrogen, and at least one of $R^V$, $R^{VI}$, $R^{VII}$ and $R^{VIII}$ is a hydrocarbyl group.

5. The sunscreen composition of claim 4, wherein said copolymer is selectively hydrogenated to provide a selectively hydrogenated copolymer.

6. The sunscreen composition of claim 4, wherein said first and second conjugated dienes are polymerized as a block copolymer comprising at least two alternating blocks:

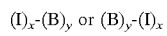

wherein:
the block (I) comprises at least one polymerized conjugated diene of formula (1);
the block (B) comprises at least one polymerized conjugated diene of formula (3);
x is the number of polymerized monomer units in block (I) and is at least 1, and
y is the number of polymerized monomer units in block (B) and is at least 25.

7. The sunscreen composition according to claim 1 wherein said polymer and/or copolymer is star-branched.

* * * * *